(12) United States Patent
Zellner et al.

(10) Patent No.: US 10,019,551 B2
(45) Date of Patent: *Jul. 10, 2018

(54) GENERATING A PATIENT-SPECIFIC ORTHOPAEDIC SURGICAL PLAN FROM MEDICAL IMAGE DATA

(71) Applicant: DEPUY SYNTHES PRODUCTS, INC., Raynham, MA (US)

(72) Inventors: Scott A. Zellner, Fort Wayne, IN (US); Gina M. Becerra, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/083,498

(22) Filed: Mar. 29, 2016

(65) Prior Publication Data

US 2016/0210412 A1 Jul. 21, 2016

Related U.S. Application Data

(63) Continuation of application No. 13/828,228, filed on Mar. 14, 2013, now Pat. No. 9,299,138.

(51) Int. Cl.
*G06K 9/00* (2006.01)
*G06F 19/00* (2018.01)
(Continued)

(52) U.S. Cl.
CPC ............ *G06F 19/321* (2013.01); *A61B 34/10* (2016.02); *G06F 19/3418* (2013.01);
(Continued)

(58) Field of Classification Search
None
See application file for complete search history.

(56) References Cited

U.S. PATENT DOCUMENTS 7,950,925 B2 5/2011 McDaniel et al.
8,265,949 B2 9/2012 Haddad
(Continued)

FOREIGN PATENT DOCUMENTS

JP 2002197200 A 7/2002
JP 2004254899 A 9/2004
(Continued)

OTHER PUBLICATIONS

European Search Report EP14158398, dated Jul. 14, 2014, 8 pages.
(Continued)

*Primary Examiner* — Nirav G Patel
(74) *Attorney, Agent, or Firm* — Barnes & Thornburg LLP

(57) ABSTRACT

Technologies for generating a patient-specific surgical plan from medical image data include receiving an orthopaedic surgical plan request from a computing device of a healthcare facility via a network, receiving a medical image of bony anatomy of a patient, and receiving constraint data corresponding to an orthopaedic surgical procedure to be performed upon the bony anatomy of the patient. Such technologies may further include determining whether the orthopaedic surgical procedure to be performed upon the bony anatomy of the patient is a difficult orthopaedic surgical procedure, generating a first surgical plan for the orthopaedic surgical procedure to be performed in response to determining that the orthopaedic procedure to be performed is not a difficult orthopaedic surgical procedure, and generating a second surgical plan for the orthopaedic surgical procedure to be performed in response to determining that the orthopaedic procedure to be performed is a difficult orthopaedic surgical procedure.

20 Claims, 6 Drawing Sheets

(51) Int. Cl.
  *A61B 34/10* (2016.01)
  *G06T 7/00* (2017.01)
  *G16H 10/60* (2018.01)
  *G16H 50/50* (2018.01)
  *A61B 34/00* (2016.01)
  *A61B 17/15* (2006.01)

(52) U.S. Cl.
  CPC ........ *G06F 19/3481* (2013.01); *G06T 7/0012* (2013.01); *G16H 10/60* (2018.01); *G16H 50/50* (2018.01); *A61B 17/154* (2013.01); *A61B 2034/108* (2016.02); *A61B 2034/252* (2016.02); *A61B 2034/256* (2016.02); *A61B 2034/258* (2016.02); *G06T 2207/30008* (2013.01)

(56) References Cited

U.S. PATENT DOCUMENTS

| | | |
|---|---|---|
| 2004/0186347 A1 | 9/2004 | Shose et al. |
| 2009/0089034 A1 | 4/2009 | Penney et al. |
| 2009/0089081 A1 | 4/2009 | Haddad |
| 2012/0209394 A1 | 8/2012 | Bojarski et al. |
| 2013/0006661 A1 | 1/2013 | Haddad |
| 2013/0018666 A1 | 1/2013 | Murphy et al. |

FOREIGN PATENT DOCUMENTS

| | | |
|---|---|---|
| JP | 2006318234 A | 11/2006 |
| JP | 2008531163 A | 8/2008 |
| JP | 2009129200 A | 6/2009 |
| WO | 2008021494 | 2/2008 |

OTHER PUBLICATIONS

Fu Xiufen et al: "Research and Implementation on CSCW-Based Workflow Management System", Apr. 26, 2007 (Apr. 26, 2007), Network and Parallel Computing; [Lecture Notes in Computer Science; Lect. Notes Computer], Springer International Publishing, CHAM, pp. 510-522, XP047403478.

European Search Report issued in connection with European Application No. 14158398.9, dated Sep. 22, 2017, 9 pages.

Notification of Reasons for Refusal, Japanese Application No. 2014-050133 (dated Mar. 20, 2018).

GENERATING A PATIENT-SPECIFIC ORTHOPAEDIC SURGICAL PLAN FROM MEDICAL IMAGE DATA

This application claims priority under 35 U.S.C. § 120 to U.S. patent application Ser. No. 13/828,228, now U.S. Pat. No. 9,299,138, which was filed on Mar. 14, 2013 and is expressly incorporated herein by reference.

TECHNICAL FIELD

The present disclosure relates generally to orthopaedic surgical procedures and, more particularly, to systems, devices, and methods for generating patient-specific orthopaedic surgical plans from medical images of the bony anatomy of patients.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses may replace a portion or the complete joint of a patient. For example, the orthopaedic prosthesis may replace the patient's knee, hip, shoulder, ankle, or other joint. In the case of a knee replacement, the orthopaedic knee prosthesis may include a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

Prior to performing an orthopaedic surgical procedure, medical images of the affected anatomy of the patient are typically taken. Based on those images and other constraints dictated by the surgical procedure to be performed, the orthopaedic surgeon typically selects an orthopaedic prosthesis and a corresponding surgical plan believed to provide the best results for the patient. However, orthopaedic surgeons are often limited to their own personal knowledge and experience when making those selections.

SUMMARY

According to one aspect, a method for generating a surgical plan for an orthopaedic surgical procedure from medical image data may include receiving an orthopaedic surgical plan request from a computing device of a healthcare facility via a network, receiving a medical image of bony anatomy of a patient, receiving constraint data corresponding to an orthopaedic surgical procedure to be performed upon the bony anatomy of the patient, and determining whether the orthopaedic surgical procedure to be performed upon the bony anatomy of the patient is a difficult orthopaedic surgical procedure based on the received medical images and the received constraint data. Additionally, the method may include generating one of a first surgical plan or a second surgical plan for the orthopaedic surgical procedure to be performed upon the bony anatomy of the patient, and transmitting at least one of the first or second surgical plans to the computing device of the healthcare facility via the network. In some embodiments, generating a first surgical plan for the orthopaedic surgical procedure to be performed upon the bony anatomy of the patient may include generating a first surgical plan for the orthopaedic surgical procedure to be performed upon the bony anatomy of the patient in response to determining that the orthopaedic procedure to be performed upon the bony anatomy the patient is not a difficult orthopaedic surgical procedure. Additionally, generating a second surgical plan for the orthopaedic surgical procedure to be performed upon the bony anatomy of the patient may include generating a second surgical plan, different from the first surgical plan, for the orthopaedic surgical procedure to be performed upon the bony anatomy of the patient in response to determining that the orthopaedic procedure to be performed upon the bony anatomy the patient is a difficult orthopaedic surgical procedure.

In some embodiments, generating a first surgical plan may include generating a first surgical plan for the orthopaedic surgical procedure to be performed upon the bony anatomy of the patient in response to determining that the orthopaedic procedure to be performed upon the bony anatomy the patient is not a difficult orthopaedic surgical procedure. Additionally, generating a second surgical plan may include generating a second surgical plan for the orthopaedic surgical procedure to be performed upon the bony anatomy of the patient in response to determining that the orthopaedic procedure to be performed upon the bony anatomy the patient is a difficult orthopaedic surgical procedure. In some embodiments, the second surgical plan is a surgical plan different from the first surgical plan.

In some embodiments, the method may further include determining patient-specific anatomical data from the medical image of the bony anatomy of the patient. Additionally, the method may include comparing the patient-specific anatomical data determined from the medical image of the bony anatomy of the patient to historical anatomical data. In some embodiments, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of comparing the patient-specific anatomical data to historical anatomical data.

Additionally or alternatively, the method may further include determining whether the patient-specific anatomical data determined from the medical image of the bony anatomy of the patient is at least one of outside of a reference range or exceeds a reference threshold. In some embodiments, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of determining that the patient-specific anatomical data is at least one of outside of the reference range or exceeds the reference threshold.

In some embodiments, the method may further include comparing a degree of femoral rotation obtained from the patient-specific anatomical data determined from the medical image of the bony anatomy of the patient. Additionally, determining whether the patient-specific anatomical data determined from the medical image of the bony anatomy of the patient is at least one of outside of a reference range or exceeds a reference threshold may include determining whether the degree of femoral rotation obtained from the patient-specific anatomical data exceeds a reference threshold degree of femoral rotation. Additionally or alternatively the method may further include comparing a tibial slope obtained from the patient-specific anatomical data determined from the medical image of the bony anatomy of the patient. In some embodiments, determining whether the patient-specific anatomical data determined from the medical image of the bony anatomy of the patient is at least one of outside of a reference range or exceeds a reference threshold may include determining whether the tibial slope obtained from the patient-specific anatomical data exceeds a reference threshold tibial slope.

Some embodiments of the method may include determining whether a complexity exists as a function of the patient-specific anatomical data determined from the medical image of the bony anatomy of the patient. Additionally, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of determining that a complexity exists. Further, determining whether a complexity exists as a function of the patient-specific anatomical data determined from the medical image of the bony anatomy of the patient may include determining at least one of whether pre-existing metal is present in a surgical area within which the orthopaedic surgical procedure is to be performed upon the bony anatomy of the patient as a function of the patient-specific anatomical data, or whether an anatomical deformation exists in the bony anatomy of the patient as a function of the patient-specific anatomical data.

In some embodiments, the method may further include transmitting the received medical image and the constraint data corresponding to the orthopaedic surgical procedure to be performed upon the bony anatomy of the patient to a remote computing device via the network, and receiving a recommendation affecting the orthopaedic surgical procedure to be performed upon the bony anatomy of the patient from the remote computing device via the network. Generating the second surgical plan for the orthopaedic surgical procedure to be performed upon the bony anatomy of the patient may include generating the second surgical plan for the orthopaedic surgical procedure to be performed upon the bony anatomy of the patient as a function of the recommendation received from the remote computing device.

The method may further include generating a notification in response to determining that the orthopaedic surgical procedure to be performed upon the bony anatomy of the patient is a difficult orthopaedic surgical procedure, and transmitting the generated notification to the computing device of the healthcare facility. Additionally, in some embodiments, receiving a medical image of bony anatomy of a patient may include receiving at least one of a radiographic image, a magnetic resonance imaging image, a computerized tomography image, or a three dimensional ultrasound image.

In some embodiments, the first and second surgical plans may include a plurality of ordered surgical steps and instructional images corresponding to the orthopaedic surgical procedure to be performed upon the bony anatomy of the patient. Additionally, the first and second surgical plans may include a recommended orthopaedic implant for use during the orthopaedic surgical procedure to be performed and/or an image including a digital template of the recommended orthopaedic implant superimposed onto the bony anatomy of the patient in the medical image. Further, the first and second surgical plans may include one or more recommended reusable instruments to use during the orthopaedic surgical procedure to be performed, one or more recommended patient-specific instruments to use during the orthopaedic surgical procedure to be performed, and/or one or more recommended single-use instruments to use during the orthopaedic surgical procedure to be performed, Additionally or alternatively, in some embodiments, the first and second surgical plans may include one or more videos of surgical procedures performed on other patients having a similar bony anatomy.

In some embodiments, receiving the orthopaedic surgical plan request from the computing device of the healthcare facility via the network may include receiving the surgical plan request from a surgeon via the computing device of the healthcare facility. Additionally, the method may further include determining whether the surgeon is a registered user of the surgical plan server, registering the surgeon as a user of the surgical plan server in response to determining that the surgeon is not a registered user, receiving surgical preference data corresponding to the surgical procedures preferences of the surgeon, and updating surgical preference data in a profile corresponding to the surgeon. Further, the method may further include receiving historical surgical procedure data corresponding to surgical procedures performed by the surgeon. Additionally, in some embodiments, the method may further include receiving surgical procedure results from the computing device of the healthcare facility via the network, and updating historical anatomical data as a function of the received surgical procedure results.

According to another aspect, a machine readable media may include a plurality of instructions stored thereon. The plurality of instructions, in response to being executed, may result in a surgical plan server receiving an orthopaedic surgical plan request from a computing device of a healthcare facility via a network, receiving a medical image of bony anatomy of a patient, receiving constraint data corresponding to an orthopaedic surgical procedure to be performed upon the bony anatomy of the patient, and determining whether the orthopaedic surgical procedure to be performed upon the bony anatomy of the patient is a difficult orthopaedic surgical procedure based on the received medical images and the received constraint data. The plurality of instructions may further result in the surgical plan server generating one of a first surgical plan or a second surgical plan for the orthopaedic surgical procedure to be performed upon the bony anatomy of the patient, and transmitting at least one of the first or second surgical plans to the computing device of the healthcare facility via the network. In some embodiments, generating a first surgical plan for the orthopaedic surgical procedure to be performed upon the bony anatomy of the patient may include generating a first surgical plan for the orthopaedic surgical procedure to be performed upon the bony anatomy of the patient in response to determining that the orthopaedic procedure to be performed upon the bony anatomy the patient is not a difficult orthopaedic surgical procedure. Additionally, generating a second surgical plan for the orthopaedic surgical procedure to be performed upon the bony anatomy of the patient may include generating a second surgical plan for the orthopaedic surgical procedure to be performed upon the bony anatomy of the patient in response to determining that the orthopaedic procedure to be performed upon the bony anatomy the patient is a difficult orthopaedic surgical procedure. In some embodiments, the second surgical plan is a customized plan different from the first surgical plan.

In some embodiments, the plurality of instructions may further result in the surgical plan server determining patient-specific anatomical data from the medical image of the bony anatomy of the patient. Additionally, the plurality of instructions may further result in the surgical plan server comparing the patient-specific anatomical data determined from the medical image of the bony anatomy of the patient to historical anatomical data. In some embodiments, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of comparing the patient-specific anatomical data to historical anatomical data.

Additionally or alternatively, the plurality of instructions may further result in the surgical plan server determining whether the patient-specific anatomical data determined from the medical image of the bony anatomy of the patient is at least one of outside of a reference range or exceeds a reference threshold. In some embodiments, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of determining that the patient-specific anatomical data is at least one of outside of the reference range or exceeds the reference threshold.

In some embodiments, the plurality of instructions may further result in the surgical plan server comparing a degree of femoral rotation obtained from the patient-specific anatomical data determined from the medical image of the bony anatomy of the patient. Additionally, determining whether the patient-specific anatomical data determined from the medical image of the bony anatomy of the patient is at least one of outside of a reference range or exceeds a reference threshold may include determining whether the degree of femoral rotation obtained from the patient-specific anatomical data exceeds a reference threshold degree of femoral rotation. Additionally or alternatively, the plurality of instructions may further result in the surgical plan server comparing a tibial slope obtained from the patient-specific anatomical data determined from the medical image of the bony anatomy of the patient. In some embodiments, determining whether the patient-specific anatomical data determined from the medical image of the bony anatomy of the patient is at least one of outside of a reference range or exceeds a reference threshold may include determining whether the tibial slope obtained from the patient-specific anatomical data exceeds a reference threshold tibial slope.

In some embodiments, the plurality of instructions may further result in the surgical plan server determining whether a complexity exists as a function of the patient-specific anatomical data determined from the medical image of the bony anatomy of the patient. Additionally, determining whether the orthopaedic surgical procedure to be performed upon the bony anatomy of the patient is a difficult orthopaedic surgical procedure may include determining whether the orthopaedic surgical procedure to be performed upon the bony anatomy of the patient is a difficult orthopaedic surgical procedure as a function of determining that a complexity exists. Further, determining whether a complexity exists as a function of the patient-specific anatomical data determined from the medical image of the bony anatomy of the patient may include determining at least one of whether pre-existing metal is present in a surgical area within which the orthopaedic surgical procedure is to be performed upon the bony anatomy of the patient as a function of the patient-specific anatomical data, or whether an anatomical deformation exists in the bony anatomy of the patient as a function of the patient-specific anatomical data.

In some embodiments, the plurality of instructions may further result in the surgical plan server transmitting the received medical image and the constraint data corresponding to the orthopaedic surgical procedure to be performed upon the bony anatomy of the patient to a remote computing device via the network, and receiving a recommendation affecting the orthopaedic surgical procedure to be performed upon the bony anatomy of the patient from the remote computing device via the network. Generating the second surgical plan for the orthopaedic surgical procedure to be performed upon the bony anatomy of the patient may include generating the second surgical plan for the orthopaedic surgical procedure to be performed upon the bony anatomy of the patient as a function of the recommendation received from the remote computing device.

The plurality of instructions may further result in the surgical plan server generating a notification in response to determining that the orthopaedic surgical procedure to be performed upon the bony anatomy of the patient is a difficult orthopaedic surgical procedure, and transmitting the generated notification to the computing device of the healthcare facility. Additionally, in some embodiments, receiving a medical image of bony anatomy of a patient may include receiving at least one of a radiographic image, a magnetic resonance imaging image, a computerized tomography image, or a three dimensional ultrasound image.

In some embodiments, the first and second surgical plans may include a plurality of ordered surgical steps and instructional images corresponding to the orthopaedic surgical procedure to be performed upon the bony anatomy of the patient. Additionally, the first and second surgical plans may include a recommended orthopaedic implant for use during the orthopaedic surgical procedure to be performed and/or an image including a digital template of the recommended orthopaedic implant superimposed onto the bony anatomy of the patient in the medical image. Further, the first and second surgical plans may include one or more recommended reusable instruments to use during the orthopaedic surgical procedure to be performed, one or more recommended patient-specific instruments to use during the orthopaedic surgical procedure to be performed, and/or one or more recommended single-use instruments to use during the orthopaedic surgical procedure to be performed, Additionally or alternatively, in some embodiments, the first and second surgical plans may include one or more videos of surgical procedures performed on other patients having a similar bony anatomy.

In some embodiments, receiving the orthopaedic surgical plan request from the computing device of the healthcare facility via the network may include receiving the surgical plan request from a surgeon via the computing device of the healthcare facility. Additionally, the plurality of instructions may further result in the surgical plan server determining whether the surgeon is a registered user of the surgical plan server, registering the surgeon as a user of the surgical plan server in response to determining that the surgeon is not a registered user, receiving surgical preference data corresponding to the surgical procedures preferences of the surgeon, and updating surgical preference data in a profile corresponding to the surgeon. Further, the plurality of instructions may also result in the surgical plan server receiving historical surgical procedure data corresponding to surgical procedures performed by the surgeon. Additionally, in some embodiments, the plurality of instructions may further result in the surgical plan server receiving surgical procedure results from the computing device of the healthcare facility via the network, and updating historical anatomical data as a function of the received surgical procedure results.

According to a further aspect, a system for generating a surgical plan for an orthopaedic surgical procedure from medical image data may include a computing device of a healthcare facility and a surgical plan server of a vendor. The computing device of the healthcare facility may be configured to generate an orthopaedic surgical plan request corresponding to an orthopaedic surgical procedure to be performed upon bony anatomy of a patient. The surgical plan server of the vendor may be configured to receive the orthopaedic surgical plan request from the computing device of the healthcare facility via a network, receive a medical image of the bony anatomy of the patient upon which the orthopaedic surgical procedure is to be performed from the computing device of the healthcare facility, receive constraint data corresponding to the orthopaedic surgical procedure to be performed upon the bony anatomy of the patient from the computing device of the healthcare facility, and determine whether the orthopaedic surgical procedure to be performed upon the bony anatomy of the patient is a difficult orthopaedic surgical procedure based on the received medical image and the received constraint data. The surgical plan server may be further configured to generate one of a first surgical plan or a second surgical plan for the orthopaedic surgical procedure to be performed upon the bony anatomy of the patient, and transmit at least one of the first or second surgical plans to the computing device of the healthcare facility via the network. In some embodiments, to generate a first surgical plan for the orthopaedic surgical procedure to be performed upon the bony anatomy of the patient may include to generate a first surgical plan for the orthopaedic surgical procedure to be performed upon the bony anatomy of the patient in response to determining that the orthopaedic procedure to be performed upon the bony anatomy the patient is not a difficult orthopaedic surgical procedure. Additionally, to generate a second surgical plan for the orthopaedic surgical procedure to be performed upon the bony anatomy of the patient may include to generate a second surgical plan for the orthopaedic surgical procedure to be performed upon the bony anatomy of the patient in response to determining that the orthopaedic procedure to be performed upon the bony anatomy the patient is a difficult orthopaedic surgical procedure. In some embodiments, the second surgical plan is a surgical plan different from the first surgical plan.

In some embodiments, the surgical plan server may be further configured to determine patient-specific anatomical data from the medical image of the bony anatomy of the patient. Additionally, the surgical plan server may further be configured to compare the patient-specific anatomical data determined from the medical image of the bony anatomy of the patient to historical anatomical data. In some embodiments, to determine whether the orthopaedic surgical procedure to be performed upon the bony anatomy of the patient is a difficult orthopaedic surgical procedure may include to determine whether the orthopaedic surgical procedure to be performed upon the bony anatomy of the patient is a difficult orthopaedic surgical procedure as a function of comparing the patient-specific anatomical data to historical anatomical data.

Additionally or alternatively, the surgical plan server may be further configured to determine whether the patient-specific anatomical data determined from the medical image of the bony anatomy of the patient is at least one of outside of a reference range or exceeds a reference threshold. In some embodiments, to determine whether the orthopaedic surgical procedure to be performed upon the bony anatomy of the patient is a difficult orthopaedic surgical procedure may include to determine whether the orthopaedic surgical procedure to be performed upon the bony anatomy of the patient is a difficult orthopaedic surgical procedure as a function of determining that the patient-specific anatomical data is at least one of outside of the reference range or exceeds the reference threshold.

In some embodiments, the surgical plan server may be further configured to compare a degree of femoral rotation obtained from the patient-specific anatomical data determined from the medical image of the bony anatomy of the patient. Additionally, to determine whether the patient-specific anatomical data determined from the medical image of the bony anatomy of the patient is at least one of outside of a reference range or exceeds a reference threshold may include to determine whether the degree of femoral rotation obtained from the patient-specific anatomical data exceeds a reference threshold degree of femoral rotation. Additionally or alternatively, the surgical plan server may be further configured to compare a tibial slope obtained from the patient-specific anatomical data determined from the medical image of the bony anatomy of the patient. In some embodiments, to determine whether the patient-specific anatomical data determined from the medical image of the bony anatomy of the patient is at least one of outside of a reference range or exceeds a reference threshold may include to determine whether the tibial slope obtained from the patient-specific anatomical data exceeds a reference threshold tibial slope.

In some embodiments, the surgical plan server may be further configured to determine whether a complexity exists as a function of the patient-specific anatomical data determined from the medical image of the bony anatomy of the patient. Additionally, to determine whether the orthopaedic surgical procedure to be performed upon the bony anatomy of the patient is a difficult orthopaedic surgical procedure may include to determine whether the orthopaedic surgical procedure to be performed upon the bony anatomy of the patient is a difficult orthopaedic surgical procedure as a function of determining that a complexity exists.

In some embodiments the system may further include a remote computing device. The remote computing device may be configured to receive the medical image and the constraint data corresponding to the orthopaedic surgical procedure to be performed upon the bony anatomy of the patient from the surgical plan server via the network, generate a recommendation affecting the orthopaedic surgical procedure to be performed upon the bony anatomy of the patient, and transmit the recommendation affecting the orthopaedic surgical procedure to be performed upon the bony anatomy of the patient to the surgical plan server via the network. Additionally, in some embodiments, the surgical plan server may be further configured to receive the recommendation affecting the orthopaedic surgical procedure to be performed upon the bony anatomy of the patient from the remote computing device. In some embodiments, to generate the second surgical plan for the orthopaedic surgical procedure to be performed upon the bony anatomy of the patient may include to generate the second surgical plan for the orthopaedic surgical procedure to be performed upon the bony anatomy of the patient as a function of the recommendation received from the remote computing device. Further, in some embodiments, the surgical plan server may be further configured to generate a notification in response to determining that the orthopaedic surgical procedure to be performed upon the bony anatomy of the patient is a difficult orthopaedic surgical procedure, and transmit the generated notification to the computing device of the healthcare facility via the network.

In some embodiments, the first and second surgical plans may include a plurality of ordered surgical steps and instructional images corresponding to the orthopaedic surgical procedure to be performed upon the bony anatomy of the patient. Additionally, the first and second surgical plans may include a recommended orthopaedic implant for use during the orthopaedic surgical procedure to be performed and/or an image including a digital template of the recommended orthopaedic implant superimposed onto the bony anatomy of the patient in the medical image. Further, the first and second surgical plans may include one or more recommended reusable instruments to use during the orthopaedic surgical procedure to be performed, one or more recommended patient-specific instruments to use during the orthopaedic surgical procedure to be performed, and/or one or more recommended single-use instruments to use during the orthopaedic surgical procedure to be performed, Additionally or alternatively, in some embodiments, the first and second surgical plans may include one or more videos of surgical procedures performed on other patients having a similar bony anatomy.

BRIEF DESCRIPTION OF THE DRAWINGS

The detailed description particularly refers to the following figures, in which.

DETAILED DESCRIPTION OF THE DRAWINGS

Figure 1:
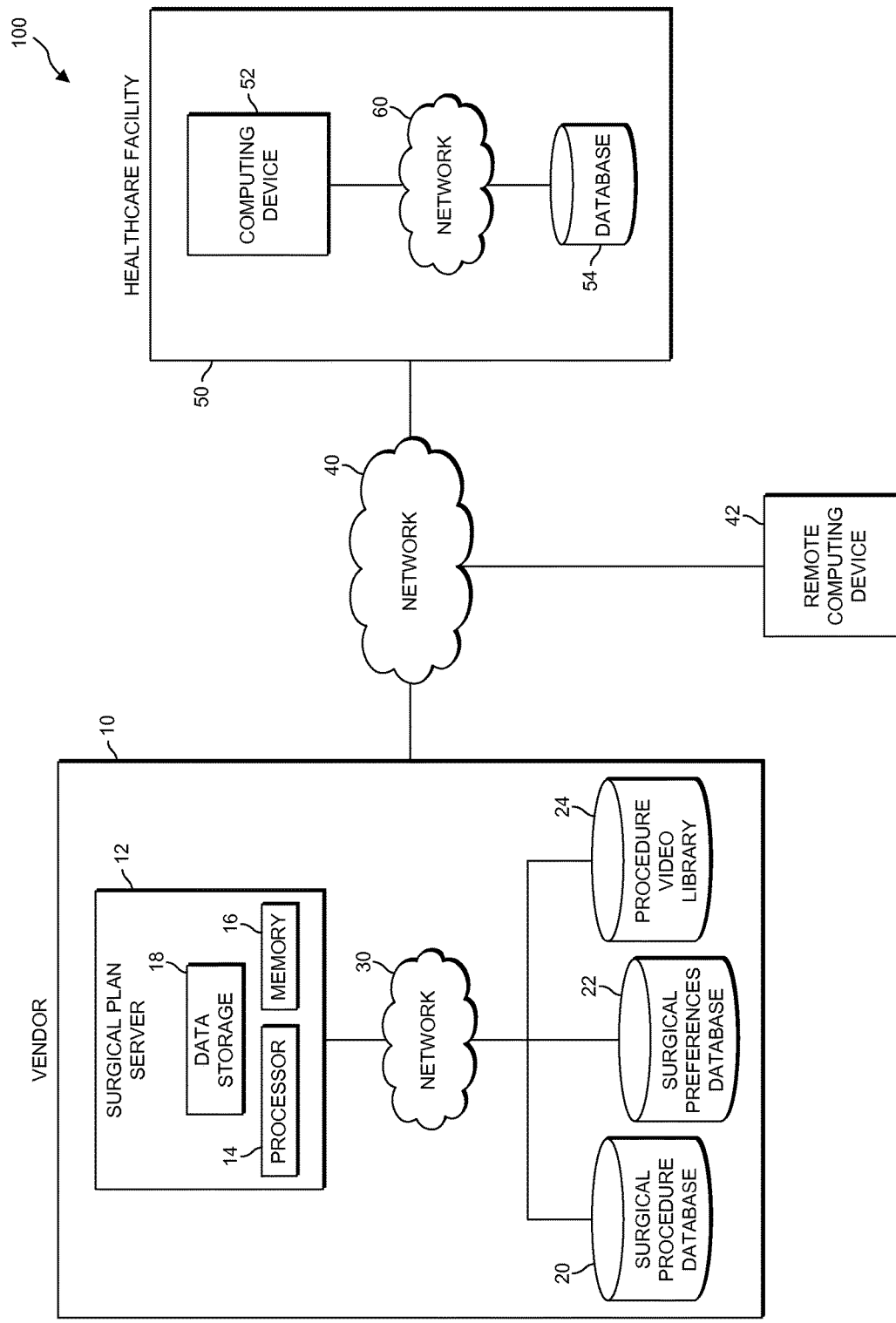
FIG. 1 is a simplified diagram of one embodiment of a system for generating an orthopaedic surgical plan from medical image data.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a system 100 for generating an orthopaedic surgical plan from medical image data includes a vendor 10, a healthcare facility 50, and a network 40 that communicatively couples the vendor 10 and the healthcare facility 50. In some embodiments, the illustrative system 100 further includes one or more remote computing devices 42. As discussed in more detail below, the vendor 10 may include a surgical plan server 12, which may generate a patient-specific surgical plan for an orthopaedic surgical procedure to be performed based at least in part, or otherwise as a function of, medical images and constraint data received from the healthcare facility 50 via the network 40.

The network 40 may be embodied as any number of various wired and/or wireless communication networks. For example, the network 40 may be embodied as or otherwise include a local area network (LAN), a wide area network (WAN), a cellular network, or a publicly-accessible, global network such as the Internet. Additionally, the network 40 may include any number of additional devices to facilitate communication between the surgical plan server 12, the computing device 52, the remote computing device 42, and/or the other computing devices.

The healthcare facility 50 may be embodied as any type of healthcare facility such as a hospital, a heath provider's office, an out patient facility, or other business or location at which healthcare services are performed or provided. The illustrative healthcare facility 50 includes a network 60, a computing device 52, and a database 54. Similar to the network 40, the healthcare facility network 60 may be embodied as any number of various wired and/or wireless communication networks. For example, the healthcare facility network 60 may be embodied as or otherwise include a local area network (LAN), a wide area network (WAN), a cellular network, or a publicly-accessible, global network such as the Internet. Additionally, the healthcare facility network 60 may include any number of additional devices to facilitate communication between the computing device 52, the database 54, and/or other computing devices of the healthcare facility 50.

The computing device 52 may display data and receive input from caregivers of the healthcare facility 50 such as, for example, doctors, nurses, anesthesiologists, and surgeons. As discussed in more detail below, a caregiver such as, for example, a surgeon may request that a patient-specific surgical plan be generated via the computing device 52. The computing device 52 may be embodied as one of a variety of different computing devices such as, for example, a desktop computer, a tablet computing device, a laptop computer, a handheld computer, a personal data assistant, a mobile phone, a server, and/or other computing devices. Of course, the healthcare facility may include additional and/or other computing devices 52 in other embodiments. Additionally, although the computing device 52 is shown in FIG. 1 as being physically located within the healthcare facility 50 in the illustrative embodiment, the computing device 52 may also be located external to the healthcare facility 50 in other embodiments. For example, in some embodiments, the computing device 52 may be located external to the healthcare facility 50 and may be configured to remotely access the healthcare facility network 60. In that way, surgeons or other caregivers may request the generation of patient-specific surgical plans from locations other than those physically located within the healthcare facility 50.

The database 54 of the healthcare facility 50 may store various types of data corresponding to patients and/or caregivers of the healthcare facility 50. For example, in some embodiments, the database maintains electronic medical records, medical images, billing information, and/or other types of information corresponding to patients of the healthcare facility 50. Additionally, the database 54 may store surgical preferences corresponding to one or more surgeons of the healthcare facility 50. Of course, the database 54 may store any other type of information corresponding to the healthcare facility 50 and/or the treatment of patients thereof.

The vendor 10 may be embodied as any type of orthopedic vendor that manufactures and/or distributes orthopedic components and/or surgical tools. The illustrative vendor 10 includes the surgical plan server 12, a vendor network 30, a surgical procedure database 20, a surgical preferences database 22, and a procedure video library 24. Similar to the network 40, the vendor network 30 may be embodied as any number of various wired and/or wireless communication networks. For example, the vendor network 30 may be embodied as or otherwise include a local area network (LAN), a wide area network (WAN), a cellular network, or a publicly-accessible, global network such as the Internet. Additionally, the vendor network 30 may include any number of additional devices to facilitate communication between the surgical plan server 12, the surgical procedure database 20, the surgical preferences database 22, the procedure video library 24, and/or other computing devices of the vendor 10.

The surgical procedure database 20 may maintain historical surgical procedure data in some embodiments. In such embodiments, the historical surgical procedure data may include data (e.g., surgical notes, orthopaedic implant sizes required, revisions required, medical images, surgical patients, patient-specific anatomical data, surgical outcomes, procedure time metrics, etc.) corresponding to surgical procedures previously performed by other surgeons. Additionally, in some embodiments, the surgical procedure database 20 may include one or more surgical procedure plans that have been branded or otherwise associated with a particular surgeon, healthcare facility, university, and/or another person or institution. As such, the one or more surgical procedure plans may include techniques perfected by other surgeons and/or institutions. Of course, it should be appreciated that the surgical procedure database 20 may maintain any other type of information corresponding to a surgical procedure that was previously performed.

The surgical preferences database 22 may maintain surgical preference data for one or more surgeons. For example, in some embodiments, the surgical preferences database 22 may include information corresponding to one or more surgical instrument preferences, surgical template preferences, surgical procedure preferences, orthopaedic implant preferences, orthopaedic implant material preferences, and/or any other type of surgical preference. Of course, it should be appreciated that the surgical preferences database 22 may maintain any other type of information corresponding to a surgical procedure that was previously performed. In some embodiments, the surgical preferences database 22 may maintain the surgical preference data in a separate profile for each surgeon utilizing the surgical plan server 12. Additionally, in some embodiments, the surgical preferences database 22 may include one or more reference anatomical thresholds and/or reference anatomical ranges. For example, in some embodiments, the surgical preferences database 22 may include a reference threshold degree or other amount of femoral rotation and/or a reference range of degrees of femoral rotation. Additionally or alternatively, the surgical preferences database 22 may include a reference degree or other amount of tibial slope and/or a reference range of degrees of tibial slope. Although the surgical preferences database 22 includes reference thresholds and/or reference ranges corresponding to the femur and the tibia in the illustrative embodiment, the surgical preferences database 22 may include reference thresholds and/or ranges corresponding to any other anatomical aspect of a patient. As discussed in more detail below, the one or more thresholds and/or ranges maintained by the surgical preferences database 22 may be used to facilitate determining whether an orthopaedic surgical procedure to be performed on a particular patient is a difficult (e.g., complex, complicated, etc.) surgical procedure to perform.

The procedure video library 24 may maintain video recordings of past surgical procedures performed by one or more surgeons. In some embodiments, the procedure video library 24 may be embodied as a database. Additionally or alternatively, the procedure video library 24 may also be embodied as a mass storage device.

The surgical plan server 12 may be embodied as any type of computing device capable of performing the functions described herein including, but not limited to, a server, a desktop computer, a laptop computer, a tablet computing device, and/or any other type of computing device. The illustrative surgical plan server 12 includes a processor 14, a memory 16, and data storage 18. Of course, the surgical plan server 12 may include other or additional components, such as those commonly found in computing devices (e.g., input/output subsystems, communication circuitry, peripheral devices, displays, etc.) in other embodiments. Additionally, in some embodiments, one or more of the illustrative components may be incorporated in, or otherwise from a portion of, another component.

The processor 14 may be embodied as any type of processor capable of performing the functions described herein. For example, the processor 14 may be embodied as a single or multi-core processor(s), a digital signal processor, a microcontroller, or other processor or processing/controlling circuit. Similarly, the memory 16 may be embodied as any type of volatile or non-volatile memory or data storage capable of performing the functions described herein. In operation, the memory 16 may store various data and software used during operation of the surgical plan server 12 such as operating systems, applications, programs, libraries, and drivers.

The data storage 18 may be embodied as any type of device or devices configured for short-term or long-term storage of data such as, for example, memory devices and circuits, memory cards, hard disk drives, solid-state drives, or other data storage devices. In some embodiments, the surgical plan server 12 may store various types of data and/or software that the processor 14 is not expected to process in the near future and/or is desirable to retain for extended periods of time.

In some embodiments, the surgical plan server 12 may communicate with the one or more remote computing device 42 over the network 40. The remote computing device 42 may be embodied as any type of computing device capable of performing the functions described herein. As such, the remote computing device 42 may include devices and structures commonly found in computing devices such as processors, memory devices, communication circuitry, and data storages, which are not shown in FIG. 1 for clarity of the description. In some embodiments, the remote computing device 42 is configured to receive medical images of an area of a patient's bony anatomy to be operated upon during an upcoming orthopaedic surgical procedure that has determined to be a complex (e.g., difficult, complicated, etc.) procedure to be performed from the surgical plan server 12 as discussed in more detail below. That is, the remote computing device 42 may receive medical images of the relevant bone or bones (and soft tissue if desired) of the patient to be operated upon. In some embodiments, the remote computing device 42 may also receive constraint data corresponding to the orthopaedic surgical procedure to be performed upon the bony anatomy of the patient from the surgical plan server 12.

Each of the remote computing devices 42 may be operated, or otherwise accessed by, one or more surgeons other than the surgeon that will perform the orthopaedic surgical procedure. For example, in some embodiments, a panel of surgeons other than the surgeon that will perform the orthopaedic surgical procedure may operate or otherwise access one or more of the remote computing devices 42. As discussed in more detail below, the one or more other surgeons and/or the panel of other surgeons may utilize the remote computing device(s) 42 to review the medical images and/or constraint data received from the surgical plan server 12 and, based on their collective (or individual) expert knowledge, may provide recommendations and/or suggestions regarding or affecting the upcoming orthopaedic surgical procedure. For example, the one or more other surgeons and/or the panel of other surgeons may provide one or more recommendations and/or suggestions (e.g., orthopaedic implant sizes, surgical templates, surgical instruments, surgical plan modifications, etc.) regarding and/or affecting how the upcoming orthopaedic surgical procedure should be performed. In embodiments wherein the one or more other surgeons and/or the panel of other surgeons provide recommendations and/or suggestions regarding or affecting the upcoming orthopaedic surgical procedure, the remote computing device(s) 42 may be configured to transmit such recommendations and/or suggestions to the surgical plan server 12 for further processing.

Additionally or alternatively, in some embodiments, the remote computing device 42, may analyze the medical images and/or constraint data received from the surgical plan server 12 to generate the one or more recommendations and/or suggestions regarding or affecting the upcoming orthopaedic surgical procedure. For example, the recommendations and/or suggestions generated by the remote computing device 42 may be embodied as one or more digital templates depicting a recommended orthopaedic implant superimposed onto the received medical images of a patient's bony anatomy in a recommended position and location. The recommendations and/or suggestions generated by the remote computing device 42 may also be embodied as one or more recommendations as to a particular type, size, and/or configuration of an orthopaedic implant and/or surgical instrument to use for the orthopaedic surgical procedure. Additionally or alternatively, the recommendations and/or suggestions may include specifications generated by the remote computing device 42 for manufacturing patient-specific (e.g., customized) surgical instruments (re-usable, single-use, etc.) for use during the orthopaedic surgical procedure. Of course, the remote computing device 42 may generate any other type recommendation or suggestion regarding how the orthopaedic surgical procedure should be performed. Regardless, the remote computing device(s) 42 may be configured to transmit such recommendations and/or suggestions to the surgical plan server 12 for further processing.

As discussed, the surgical plan server 12 may generate a patient-specific surgical plan for an orthopaedic surgical procedure to be performed on a patient in response to a request received from the computing device 52 of the healthcare facility 50. In some embodiments, the patient-specific surgical plan may be generated based at least in part on medical images and constraint data corresponding to the relevant bone or bones (and soft tissue if desired) of a patient to be operated upon. For example, as discussed in more detail below, the surgical plan server 12 may analyze the medical images to determine patient-specific anatomical data of the affected anatomy (e.g., the relevant bone or bones) upon which the upcoming orthopaedic surgical procedure is to be performed. Based on the patient-specific anatomical data of the affected anatomy, the constraint data, and historical surgical procedure data, the surgical plan server 12 may determine whether the orthopaedic surgical procedure to be performed is a difficult surgical procedure to perform. In some embodiments, in response to determining that the orthopaedic surgical procedure to be performed is not a difficult procedure to perform, the surgical plan server 12 may generate a surgical plan consistent with the generally accepted surgical procedures and/or standards corresponding to the particular type of surgical procedure to be performed. If, however, it is instead determined that the orthopaedic surgical procedure to be performed is a difficult procedure to perform, the surgical plan server 12 may notify the surgeon of the potential difficulties. As discussed below, in some embodiments, the surgical plan server 12 may generate a customized patient-specific surgical plan for difficult surgical procedures based at least in part on a recommendation received from one or more other surgeons. In such embodiments, the customized patient-specific surgical plan generated for the difficult surgical procedure may be different from the surgical plan generated for non-complicated procedures. That is, because of the complexities that will be encountered, a customized patient-specific surgical plan generated for a difficult surgical procedure may include extra and/or modified steps compared to surgical plans that are generated for non complicated procedures.

Figure 2:
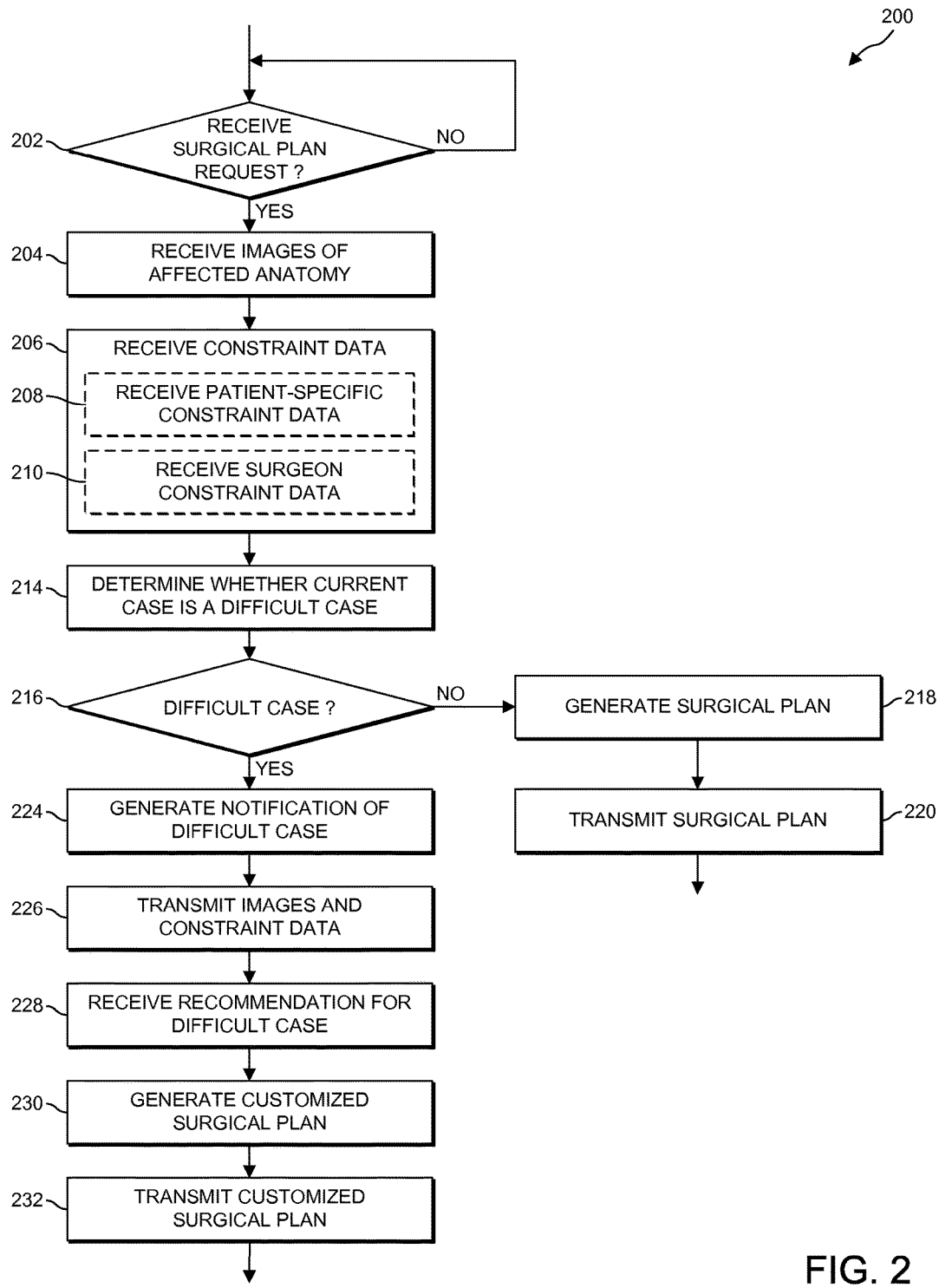
FIG. 2 is a simplified flow diagram of one embodiment of a method that may be executed by the surgical plan server of FIG. 1 for generating an orthopaedic surgical plan from medical image data.

Referring now to FIG. 2, in use, the surgical plan server 12 may execute a method 200 for generating a patient-specific orthopaedic surgical plan from medical image data received from the healthcare facility 50. The method 200 begins with block 202 in which the surgical plan server 12 determines whether a request to generate a patient-specific surgical plan has been received by the healthcare facility 50. In some embodiments, the request to generate a patient-specific surgical plan may be received from the computing device 52 of the healthcare facility 50 via the network 40. The request may include any data relevant to the surgical plan being requested, any data related to the orthopaedic surgical procedure to be performed, any data related to the patient on which the orthopaedic surgical procedure to be performed, and/or any other data useful for customizing the orthopaedic surgical procedure to the patient. For example, the request data may include, but is not limited to, the type of orthopaedic surgical procedure to be performed, the type of orthopaedic implant to be used, rendered images of the relevant anatomical portions of the patient, digital templates of the orthopaedic implants and/or planned resection lines, pre-operative notes, diagrams, historic patient data, X-rays, medical images, patient medical records, patient identification data, and/or any other data useful for customizing the orthopaedic surgical procedure to the patient. If, in block 202, the surgical plan server 12 determines that a patient-specific surgical plan request has been received, the method 200 advances to block 204. If, in block 202, the surgical plan server 12 determines instead that a patient-specific surgical plan request has not been received, the method 200 returns to block 202 to continue monitoring for the receipt of a request for generation of a patient-specific surgical plan.

In block 204, the surgical plan server 12 receives medical images of the affected anatomy of the patient from the healthcare facility 50. Typically, such medical images are generated pre-operatively in preparation for an orthopaedic surgical procedure. The medical images may include any number of medical images of various types. For example, the medical images may include a medical image of the relevant bone(s) taken along the sagittal plane of the patient's body and a medical image of the relevant bone(s) taken along the coronal plane of the patient's body. The medical images may include X-ray images, magnetic resonance imaging (MRI) images, computerized tomography (CT) images, and/or any other type of image capable of providing indicia of the relevant bone or bones. Such imaging devices may be located in the healthcare facility 50 or may be located remote therefrom. The imaging devices may or may not be communicatively coupled to the healthcare facility 50. After receiving the medical images of the affected anatomy of the patient from the healthcare facility 50, the method 200 advances to block 206.

In block 206, the surgical plan server 12 may receive constraint data corresponding to the orthopaedic surgical procedure to be performed. The constraint data may limit, restrict, or otherwise affect the generation of the surgical plan for the patient. In some embodiments, in block 208, the surgical plan server 12 may receive patient-specific constraint data. The patient-specific constraint data may include one or more patient medical records, planned resection lines, historic patient data, patient identification data (e.g., age, gender, activity level, etc.), and/or any other data corresponding to the patient. Additionally or alternatively, in block 210, the surgical plan server 12 may receive surgeon constraint data. The surgeon constraint data may include the surgeon's preference for an orthopaedic implant type, the surgeon's preference for particular parts of the implant, the degree of acceptable orthopedic implant sizes (e.g., a restriction on the range of implant sizes that may be recommended), the amount of bone that will be resected, the surgeon's preferred type of surgical plans, the planned location and/or orientation of the orthopaedic implant, fixation type (e.g., cement or cementless), material type, finish, and other features such as head size and other preferences such as metal-on-metal, metal-on-ceramic, ceramic-on-ceramic, metal-on-poly, or the like. After receiving the constraint data corresponding to the orthopaedic surgical procedure to be performed, the method 200 advances to block 214.

Figure 3:
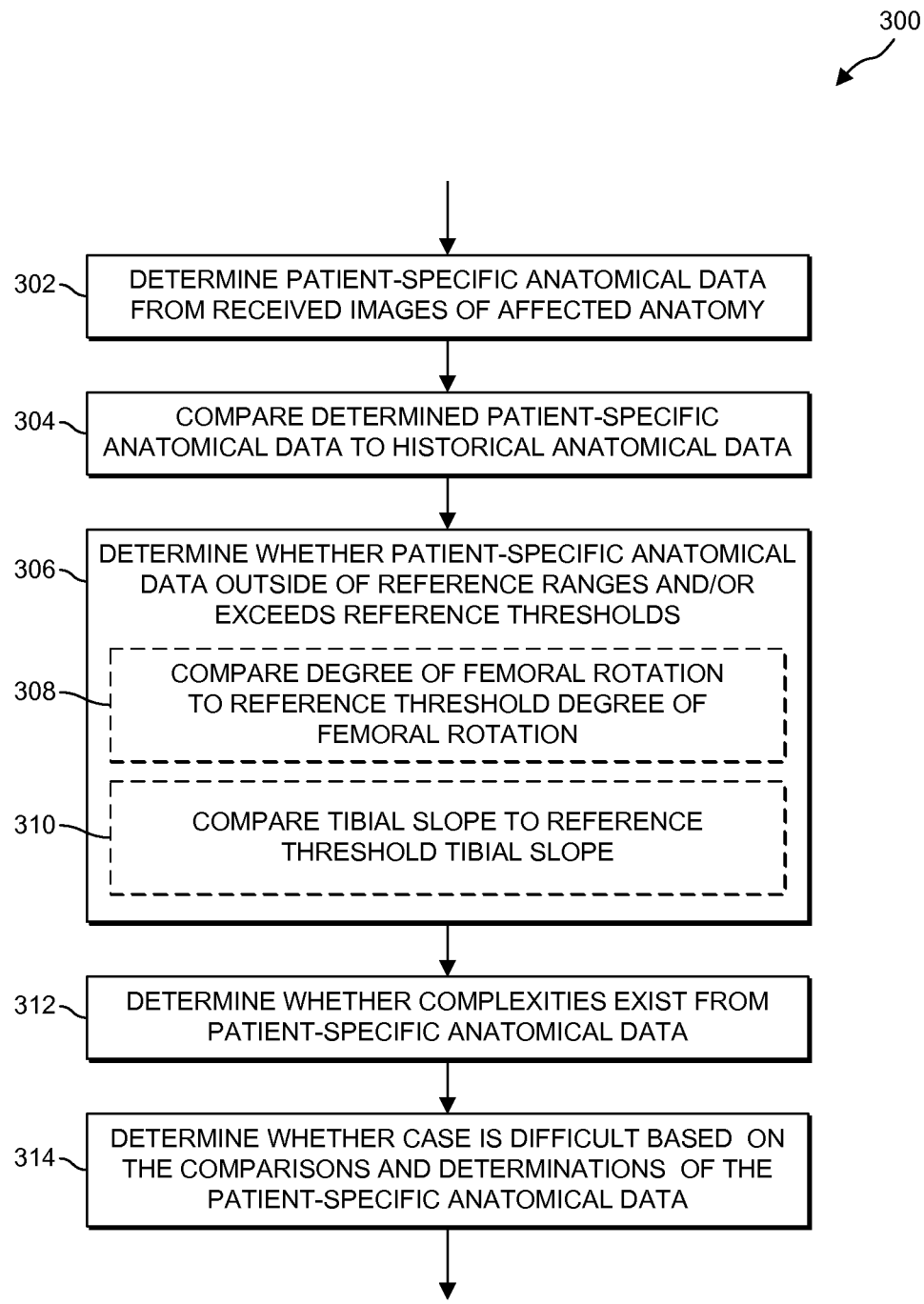
FIG. 3 is a simplified flow diagram of one embodiment of a method that may be executed by the surgical plan server of FIG. 1 for determining whether an orthopaedic surgical procedure to be performed upon bony anatomy of a patient is a difficult orthopaedic surgical procedure.

In block 214, the surgical plan server 12 determines whether the orthopaedic surgical procedure to be performed is a difficult orthopaedic surgical procedure to perform. To do so, the surgical plan server 12 may execute a method 300 for determining whether an orthopaedic surgical procedure to be performed upon the bony anatomy of a patient is a difficult orthopaedic surgical procedure to perform as shown in FIG. 3. The method 300 beings with block 302 in which the surgical plan server 12 determines or otherwise obtains patient-specific anatomical data from the medical images received from the healthcare facility 50 that depict an affected portion of a patient's bony anatomy (e.g., the relevant bone or bones upon which an orthopaedic surgical procedure is to be performed). To do so, the surgical plan server 12 may determine relevant aspects of the patient's bone or bony anatomy from the medical images. For example, the surgical plan server 12 may analyze the medical images to determine one or more mechanical axis of the relevant bones, determine one or more resection planes of the relevant bones, locate particular features of the relevant bones, determine a degree of femoral rotation, determine a degree of tibial slope, determine whether pre-existing metal or other foreign objects are present in the affected portion of the patient's bony anatomy, determine whether an anatomic deformation exists in the affected portion of the patient's bony anatomy, and/or the like. In some embodiments, the surgical plan server 12 may perform an image analysis procedure (e.g., feature detection, edge detection, computer vision, machine vision, etc.) on the medical images to detect an object or an area of interest and/or determine the relevant aspects of the patient's bone or bony anatomy. Of course, it should be appreciated that the surgical plan server 12 may use any other procedure suitable for obtaining, determining, or otherwise extracting the relevant aspects of the patient's bone or bony anatomy from the medical images. After determining the patient-specific anatomical data from the medical images, the method 300 advances to block 304.

In block 304, the surgical plan server 12 compares the patient-specific anatomical data to historical anatomical data. For example, in some embodiments, the surgical plan server 12 may compare the patient-specific anatomical data determined from the medical images to historical anatomical data maintained in the surgical procedure database 20. The historical anatomical data maintained in the surgical procedure database 20 may include relevant aspects of other patients' bony anatomy obtained from medical images received in connection with other orthopaedic surgical procedures that are to be performed and/or have already been performed. In some embodiments, the surgical plan server 12 may compare the patient-specific anatomical data to the historical anatomical data to determine whether the bony anatomy of the patient upon which the orthopaedic surgical procedure is to be performed is similar to the bony anatomy of another patient (e.g., a present or past patient). Of course, the surgical plan server 12 may perform any other type of comparison between the patient-specific anatomical data corresponding to the patient upon which the orthopaedic surgical procedure is to be performed and historical anatomical data corresponding to other patients.

In block 306, the surgical plan server 12 may determine whether the patient-specific anatomical data meets or exceeds one or more reference thresholds and/or falls outside of one or more reference ranges. To do so, the surgical plan server 12 may compare the patient-specific anatomical data determined from the medical images to the one or more reference thresholds and/or reference ranges maintained in the surgical preferences database 22. For example, the surgical plan server 12, in block 308, may compare the degree of femoral rotation determined from the medical images with the reference degree of femoral rotation in some embodiments. In such embodiments, the surgical plan server 12 may thereafter determine whether the degree of femoral rotation determined from the medical images exceeds the reference degree of femoral rotation. In some embodiments, the surgical plan server 12 in block 310 may compare the degree of tibial slope determined from the medical images with the reference degree of tibial slope. In such embodiments, the surgical plan server 12 may thereafter determine whether the degree of tibial slope determined from the medical images exceeds the reference degree of tibial slope.

In block 312, the surgical plan server 12 may determine whether any complexities exist in the patient-specific anatomical data determined from the medical images. As discussed, the surgical plan server 12 may determine from the medical images whether any pre-existing metal and/or other foreign objects are present in the affected portion of the patient's bony anatomy. Additionally, the surgical plan server 12 may determine from the medical images whether an anatomic deformation exists in the affected portion of the corresponding patient's bony anatomy. In such embodiments, the surgical plan server 12 may determine in block 312 that complexities exist from the patient-specific anatomical data. Although the surgical plan server 12 of the illustrative embodiment determines that complexities exist from the patient-specific anatomical data in response to determining that pre-existing metal, a foreign object, and/or a deformity exists, it should be appreciated that the surgical plan server 12 may determine that complexities exist from any other type of patient-specific anatomical data in other embodiments.

In block 314, the surgical plan server 12 may determine whether the surgical procedure to be performed is a difficult surgical procedure to perform based on the prior analysis. In some embodiments, the surgical plan server 12 may determine that the surgical procedure to be performed is a difficult procedure based at least in a part on, or otherwise as a function of, comparing the patient-specific anatomical data determined from the medical images to the historical anatomical data as discussed above. For example, in embodiments wherein the surgical plan server 12 determines that the bony anatomy of the patient upon which the orthopaedic surgical procedure is to be performed is similar to the bony anatomy of another patient that previously underwent a similar orthopaedic surgical procedure, the surgical plan server 12 may determine that the orthopaedic surgical procedure to be performed is a difficult surgical procedure to perform based on determining that the previous orthopaedic surgical procedure was difficult. Additionally or alternatively, the surgical plan server 12 may determine in block 314 that the surgical procedure to be performed is a difficult surgical procedure to perform based at least in a part on determining that the patient-specific anatomical data (e.g., the degree of femoral rotation, the degree of tibial slope, etc.) exceeds the reference thresholds (e.g., the reference degree of femoral rotation and/or the reference degree of tibial slope) and/or is outside of the reference ranges. In block 314, the surgical plan server 12 may also determine that the surgical procedure to be performed is a difficult surgical procedure to perform based at least in a part on determining that pre-existing metal, a foreign object, and/or a deformity exists in the affected portion (or the planned surgical area) of the patient's bony anatomy. Of course, the surgical plan server 12 may use any other criteria for determining whether the orthopaedic surgical procedure to be performed is a difficult (e.g., complex, complicated, etc.) surgical procedure to perform.

Referring now back to FIG. 2, if in block 216, the surgical plan server 12 determines that the orthopaedic surgical procedure to be performed is a difficult orthopaedic surgical procedure to perform, the method 200 advances to block 224 discussed below. If, however, the surgical plan server 12 instead determines in block 216 that the orthopaedic surgical procedure to be performed is not a difficult orthopaedic surgical procedure to perform, the method 200 advances to block 218.

In block 218, the surgical plan server 12 generates a surgical plan based on the medical images and the constraint data received from the healthcare facility 50. In some embodiments, the surgical plan generated by the surgical plan server 12 may include one or more instructions or procedures describing and/or depicting individual surgical steps that should be performed by the surgeon during the orthopaedic surgical procedure. The surgical plan server 12 may select the one or more instructions or procedures describing and/or depicting the individual surgical steps to be performed the surgeon based at least in part on, or otherwise as a function of, the medical images and constraint data received from the healthcare facility 50, the particular surgeon performing the orthopaedic surgical procedure, the particular type of orthopaedic surgical procedure to be performed, and/or surgical procedures or techniques perfected by other surgeons for the particular type of orthopaedic surgical procedure to be performed. In embodiments wherein the surgical plan includes surgical procedures and/or techniques perfected by other surgeons for the particular type of orthopaedic surgical procedure to be performed, the surgical plan server 12 may retrieve the surgical procedures and/or techniques perfected by other the surgeons from the surgical procedure database 20. In some embodiments, the surgical plan generated by the surgical plan server 12 may also include one or more videos and/or images of similar surgical procedures performed by other surgeons. In embodiments wherein the surgical plan includes videos of similar surgical procedures, the surgical plan server 12 may retrieve the one or more videos from the procedure video library 24.

Additionally, in some embodiments, the surgical plan generated by the surgical plan server 12 may include an estimated amount of time needed to complete all or a portion of the orthopaedic surgical procedure to be performed. In such embodiments, the surgical plan server 12 may be configured to estimate the amount needed to complete all of a portion of a particular orthopaedic surgical procedure to be performed based at least in part on, or otherwise as a function of, the historical surgical procedure data maintained in the surgical procedure database 20. As discussed, the historical surgical procedure data maintained in the surgical procedure database 20 may include procedure time metrics, which may embody the amount of time that a previously performed orthopaedic surgical procedure (or a portion thereof) took to complete. In such embodiments, the surgical plan server 12 may determine an estimated amount of time for the orthopaedic surgical procedure to be performed based at least in part on the procedure time metrics corresponding to substantially similar orthopaedic surgical procedures that were previously preformed.

In some embodiments, the surgical plan generated by the surgical plan server 12 may also include a recommendation of an orthopaedic implant type and size for use with relevant bone(s) of the patient. To do so, the surgical plan server 12 may perform a digital templating procedure on the medical images received from the healthcare facility 50 to determine the orthopaedic implant to recommend to the surgeon or the healthcare facility 50 for use with the relevant bone(s) of the patient. For example, the digital templating procedure performed on the medical images by the surgical plan server 12 may be similar to those digital templating procedures described in U.S. Patent Application Publication No. 2009/0089081 incorporated by reference in its entirety herein.

Additionally or alternatively, the surgical plan server 12 may select the appropriate orthopaedic implant type and size that satisfies the constraint data received from the healthcare facility 50.

Figure 6:
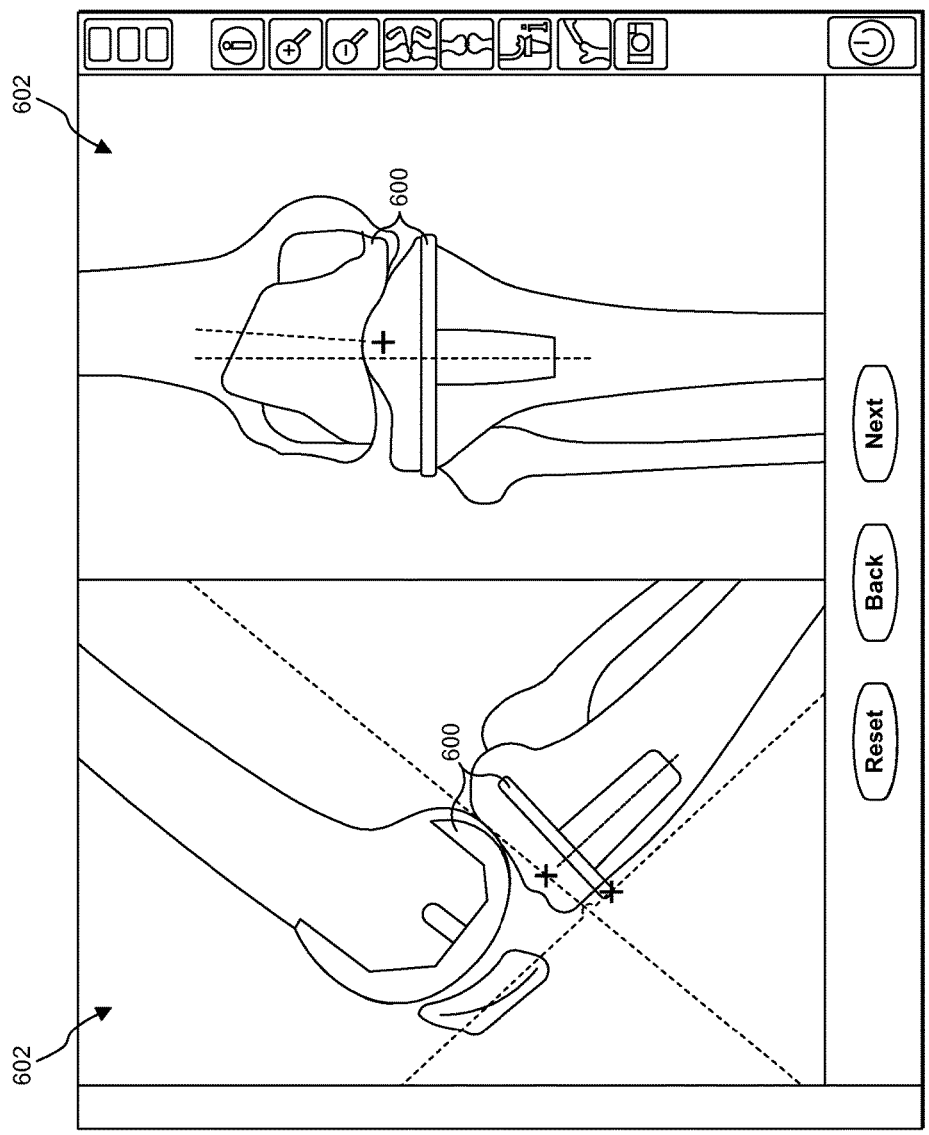
FIG. 6 is a simplified diagram showing a medical image having a digital template of an orthopaedic implant superimposed thereon.

In some embodiments, the surgical plan generated by the surgical plan server 12 may include copies the resultant images used to performed digital templating performed on the medical images received from the healthcare facility 50, in addition to the orthopaedic implant recommended based on the digital templating procedure. For example, in one illustrative embodiment, as illustrated in FIG. 6, surgical plan server 12 may generate a surgical plan that includes a digital template 600 of a recommended orthopaedic implant superimposed on a medical image 602 of a bone of the patient. Although the illustrative digital template 600 is illustrated as a two-dimensional template, in other embodiments, the digital template may include any number of two-dimensional and/or three-dimensional electronic renderings of the recommended orthopaedic implant.

Additionally, in some embodiments, the surgical plan generated by the surgical plan server 12 may include a listing of orthopaedic surgical materials, products, and/or instruments needed to perform the orthopaedic surgical procedure. For example, the generated surgical plan may include a materials list indicating one or more orthopaedic surgical implants, drill/pin guides, tibial cutting guide blocks, femoral cutting guide blocks, alignment guides, and/or templates required to complete the orthopaedic surgical procedure. Of course, it should be appreciated that the materials list may include any orthopaedic surgical material, product, and/or instrument needed to perform the orthopaedic surgical procedure.

Additionally or alternatively, in some embodiments, the surgical plan may include information indicative of a single-use kit that may be provided by the vendor 10 for use during the orthopaedic surgical procedure. In such embodiments, the single-use kit may include one or more single-use (e.g., one-time, single-procedure, single-patient, etc.) materials, products, and/or instruments needed to complete the orthopaedic surgical procedure, but may be disposed after the orthopaedic surgical procedure. For example, the single-use kit may include a specific orthopaedic implant determined for use with a particular patient and one or more patient-specific, single-use orthopaedic surgical implants, single-use drill/pin guides, single-use tibial cutting guide blocks, single-use femoral cutting guide blocks, single-use alignment guides, and/or single-use templates required to complete the orthopaedic surgical procedure on the particular patient. Of course, it should be appreciated that the single-use kit may include any other type of single-use orthopaedic surgical material, product, and/or instrument needed to perform the orthopaedic surgical procedure. It should be further appreciated that the single-use surgical materials, products, and/or instruments included within the single-use kit are patient-specific and, as a result, are customized for the particular patient.

Referring back to FIG. 2, regardless of the specific content of the surgical plan, the surgical plan server 12, in block 220, may transmit the generated surgical plan to the healthcare facility 50 via the network 40. In some embodiments, the surgical plan server 12 may transmit the generated surgical plan to the computing device 52 located in the healthcare facility 50 for review by the surgeon.

Referring back to block 216, in response to determining that the orthopaedic surgical procedure to be performed is a difficult orthopaedic surgical procedure to perform, the method 200 advances to block 224 in which the surgical plan server 12 generates a notification message to inform the surgeon that the orthopaedic surgical procedure to be performed is difficult. In such embodiments, the surgical plan server 12 may transmit the notification message to the healthcare facility 50 via the network 40. In some embodiments, the surgical plan server 12 may transmit the notification message to the computing device 52 located in the healthcare facility 50 to be displayed to the surgeon.

In some embodiments, in block 226, the surgical plan server 12 may also transmit the medical images and the constraint data to the remote computing device(s) 42 in response to determining that the orthopaedic surgical procedure to be performed is a difficult orthopaedic surgical procedure to perform. In such embodiments, one or more surgeons other than the surgeon that will perform the upcoming orthopaedic surgical procedure may provide one or more recommendations and/or suggestions regarding or affecting the upcoming orthopaedic surgical procedure based on the medical images and/or constraint data received from the surgical plan server 12. For example, the one or more surgeons (e.g., a panel of surgeons) may review the medical images and/or constraint data received from the surgical plan server 12 and, based on their expert knowledge, may provide recommendations and/or suggestions (e.g., a recommended procedure, a recommended orthopaedic implant, a size or a range of sizes of an orthopaedic implant to use, recommended surgical instruments, recommended guides or templates to use, an amount of bone that should be resected, a recommended location and/or orientation of bone that should be resected, a recommended location and/or orientation of an orthopaedic implant, a fixation type for an orthopaedic implant, warnings, etc.) regarding the orthopaedic surgical procedure to be performed on the relevant bone or bones (and/or the soft tissue) of the patient. Of course, it should be appreciated that the recommendations and/or suggestions provided by the other surgeons may include any other type or recommendation, suggestion, and/or information corresponding to and/or affecting the orthopaedic surgical procedure to be performed. Additionally, the one or more recommendations and/or suggestions affecting the orthopaedic surgical procedure to be performed may be generated by the remote computing device 42 itself. In some embodiments, the remote computing device 42 may transmit the one or more recommendations and/or suggestions provided by the other surgeons (and/or the panel of other surgeons) to the surgical plan server 12 via the network 40.

In block 228, the surgical plan server 12 receives the one or more recommendations and/or suggestions regarding the difficult orthopaedic surgical procedure to be performed from the remote computing device(s) 42. In some embodiments, the surgical plan server 12 receives the one or more suggestions and/or recommendations from the remote computing device(s) 42 via the network 40. After receiving the suggestions and/or recommendations regarding the difficult orthopaedic surgical procedure to be performed, the method 200 advances to block 230.

In block 230, the surgical plan server 12 generates a customized patient-specific surgical plan for the difficult orthopaedic surgical procedure to be performed on the relevant bony anatomy (e.g., the relevant bone or bones) of the patient based on the medical images and constraint data received from the healthcare facility 50, as well as the one or more suggestions and/or recommendations provided by the other surgeons via the remote computing device 42. To do so, the surgical plan server 12 may generate the customized patient-specific surgical plan for the difficult orthopaedic surgical procedure to be performed using procedures similar to those discussed above for generating surgical plans for orthopaedic surgical procedures not determined to be difficult to perform with regard to block 218. However, in generating the customized patient-specific surgical plan for the difficult orthopaedic surgical procedure to be performed, the surgical plan server 12 may factor in the one or more recommendations and/or suggestions provided by the other surgeons via the remote computing device 42. In that way, the surgical plan server 12 generates a customized patient-specific surgical plan for the difficult orthopaedic surgical procedure to be performed. After generating the customized patient-specific surgical plan for the difficult orthopaedic surgical procedure to be performed, the method 200 advances to block 232 in which the surgical plan server 12 transmits the generated customized patient-specific surgical plan to the healthcare facility 50 via the network 40. In some embodiments, the surgical plan server 12 may transmit the customized patient-specific surgical plan to the computing device 52 located in the healthcare facility 50 for review by the surgeon that will perform the upcoming orthopaedic surgical procedure.

Figure 4:
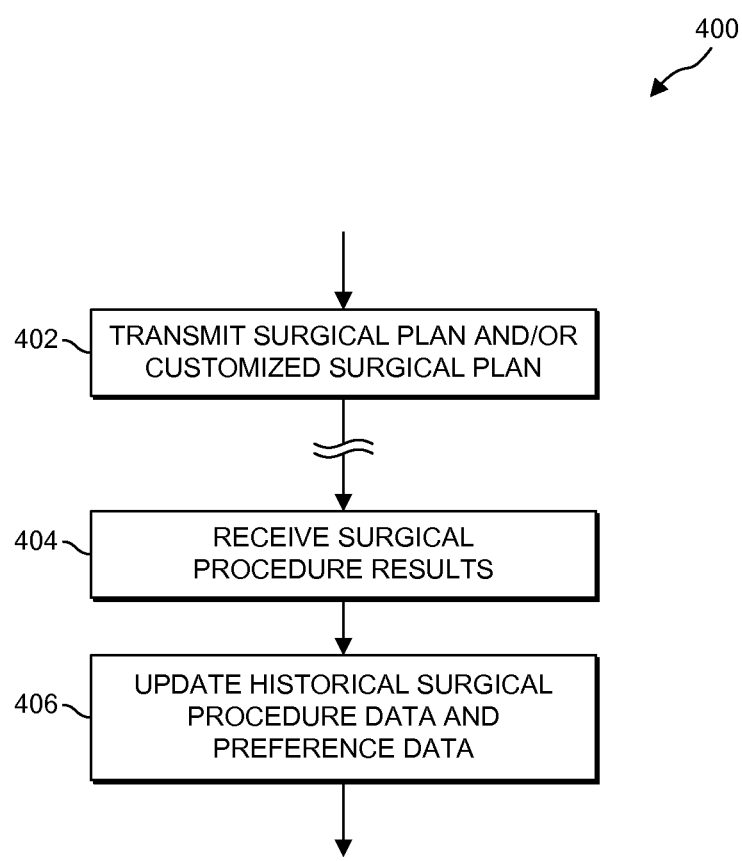
FIG. 4 is a simplified flow diagram of one embodiment of a method that may be executed by the surgical plan server of FIG. 1 for updating historical surgical procedure data.

Referring now to FIG. 4, in use, the surgical plan server 12 may execute a method 400 updating historical surgical procedure data. The method 400 beings with block 402 in which the surgical plan server 12 transmits a patient-specific surgical plan and/or a customized patient-specific surgical plan (e.g., for difficult orthopaedic surgical procedures) to the healthcare facility 50 and/or the computing device 52 of the healthcare facility 50.

Subsequently, in block 404, the surgical plan server 12 receives one or more surgical results and/or outcomes of the orthopaedic surgical procedure performed by the surgeon. In some embodiments, the surgical results and/or outcomes of the orthopaedic surgical procedure may include surgical notes (preoperative, postoperative, etc.), information corresponding to necessary deviations from the surgical plan, images taken during the orthopaedic surgical procedure, videos recorded during the orthopaedic surgical procedure, sound recordings taken during the orthopaedic surgical procedure, medical images taken during the orthopaedic surgical procedure, and/or any other type of information describing or illustrating the performance of the orthopaedic surgical procedure. After receiving the surgical procedure results and/or outcomes of the orthopaedic surgical procedure performed by the surgeon, the method 400 advances to block 406.

In block 406, the surgical plan server 12 may update the historical surgical procedure data and/or the surgical preferences data with the one or more surgical results and/or outcomes received for the orthopaedic surgical procedure performed by the surgeon. To do so, the surgical plan server 12 may update the surgical procedure database 20 and/or the surgical preferences database 22 to include the one or more surgical results and/or outcomes. In that way, the one or more surgical results and/or outcomes may be used to facilitate generating surgical plans and/or determining the level of difficulty of subsequent orthopaedic surgical procedures that are to be performed on other patients (or subsequent procedures on the same patient).

Figure 5:
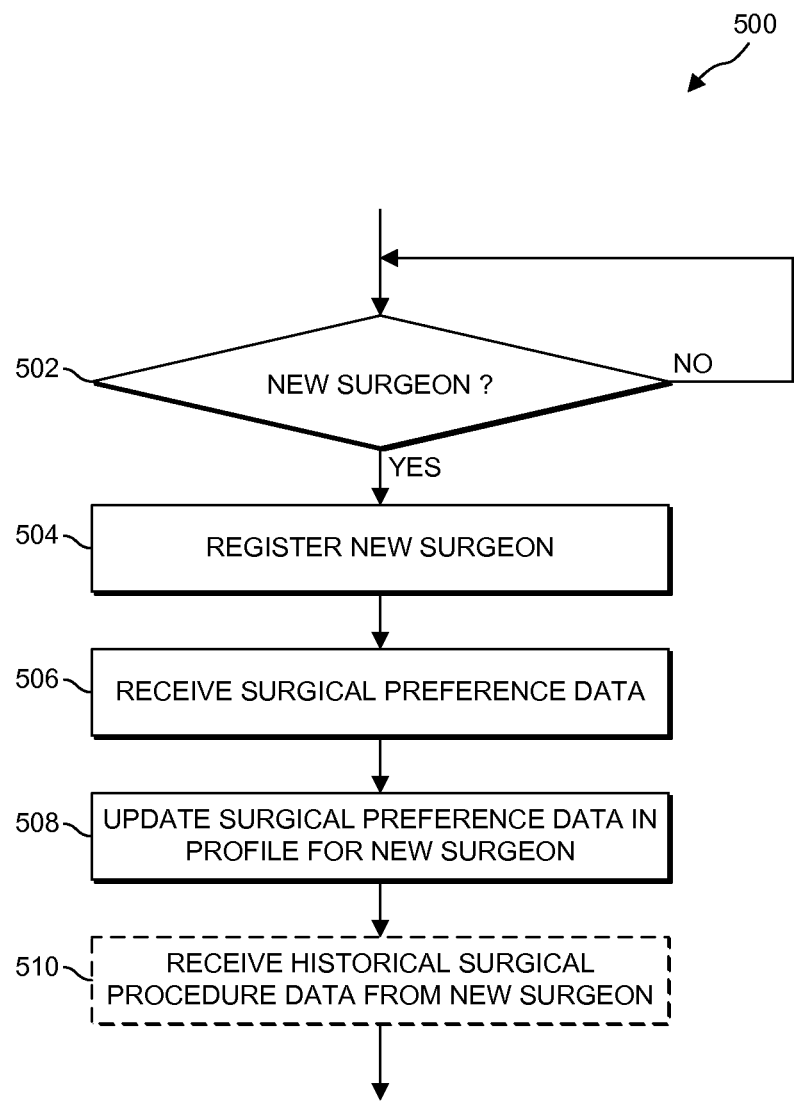
FIG. 5 is a simplified flow diagram of one embodiment of a method that may be executed by the surgical plan server of FIG. 1 for registering a new user.

Referring now to FIG. 5, in use, the surgical plan server 12 may execute a method 500 for registering a new user. The method 500 begins with block 502 in which the surgical plan server 12 determines whether a surgeon (e.g., a user) of the surgical plan server 12 is new surgeon (e.g., a new user). To do so, the surgical plan server 12 may determine whether a surgeon requesting generation of a new patient-specific surgical plan is a new user or an existing user of the surgical plan server 12. In some embodiments, the surgical plan server 12 may determine whether the surgeon is a new user based on or otherwise as a function of user logon information (e.g., username, password, and/or any other type of credential) received from the surgeon via the computing device 52. If, in block 502, the surgical plan server 12 determines that the surgeon is a new surgeon (e.g., a new user), the method 500 advances to block 504. If, however, the surgical plan server 12 determines that the surgeon is an existing surgeon (e.g., an existing user), the method 500 returns to block 502 to monitor for new surgeon users.

In block 504, the surgical plan server 12 registers the new surgeon as a user. To do so, the surgical plan server 12 may generate a new account for the surgeon. Additionally, in some embodiments, the surgical plan server 12 may generate a profile for the surgeon. In such embodiments, the profile generated for the surgeon may be maintained by the surgical preferences database 22. Of course, it should be appreciated that the surgical plan server 12 may perform any other procedure and/or operation typical for registering a new user to a system.

In block 506, the surgical plan server 12 may receive surgical preference data from the new surgeon. The received surgical preference data may include one or more the surgeon's preferences for orthopaedic implant types, the surgeon's preferences for particular parts of implants or surgical procedures, the degree of acceptable orthopedic implant sizes (e.g., a restriction on the range of implant sizes that may be recommended), the surgeon's preferences for fixation types (e.g., cement or cementless), material types, finishes, and other features such as head sizes and other preferences such as metal-on-metal, metal-on-ceramic, ceramic-on-ceramic, metal-on-poly, or the like.

In block 508, the surgical plan server 12 may update the profile created for the new surgeon to include the surgical preference data received from the new surgeon. To do so, the surgical plan server 12 may update the profile corresponding to the new surgeon in the surgical preferences database 22.

In some embodiments, in block 510, the surgical plan server 12 may receive historical surgical procedure data from the newly registered surgeon. The historical surgical procedure data received from the newly registered surgeon may include one or more surgical results and/or outcomes corresponding to orthopaedic surgical procedures previously performed by the surgeon. For example, the one or more surgical results and/or outcomes received from the newly registered surgeon may include one or more surgical notes (preoperative, postoperative, etc.), information corresponding to necessary deviations from previous surgical plans, images taken during previous orthopaedic surgical procedures, videos recorded during previous orthopaedic surgical procedures, sound recordings taken during previous orthopaedic surgical procedures, medical images taken during previous orthopaedic surgical procedures, and/or any other type of information describing or illustrating an orthopaedic surgical procedure previously performed by the surgeon. In some embodiments, the surgical plan server 12 may update the historical surgical procedure data in the surgical procedure database 20 with the one or more surgical results and/or outcomes received from the newly registered surgeon. In that way, the one or more surgical results and/or outcomes may be used to facilitate generating surgical plans and/or determining the level of difficulty of subsequent orthopaedic surgical procedures that are to be performed on patients.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. A method for generating a surgical plan for an orthopaedic surgical procedure by a surgical plan server of a vendor from medical image data, the method comprising:
   receiving an orthopaedic surgical plan request from a computing device of a healthcare facility via a network;
   receiving a medical image of bony anatomy of a patient;
   receiving constraint data corresponding to an orthopaedic surgical procedure to be performed upon the bony anatomy of the patient;
   determining, by the surgical plan server automatically in response to receiving the medical images and the constraint data, whether the orthopaedic surgical procedure to be performed upon the bony anatomy of the patient is a difficult orthopaedic surgical procedure based on the received medical images and the received constraint data;
   automatically generating, by the surgical plan server, one of: (i) a first surgical plan for the orthopaedic surgical procedure to be performed upon the bony anatomy of the patient in response to determining that the orthopaedic procedure to be performed upon the bony anatomy the patient is not a difficult orthopaedic surgical procedure; or (ii) a second surgical plan, different from the first surgical plan, for the orthopaedic surgical procedure to be performed upon the bony anatomy of the patient in response to determining that the orthopaedic procedure to be performed upon the bony anatomy the patient is a difficult orthopaedic surgical procedure; and
   transmitting at least one of the first or second surgical plans to the computing device of the healthcare facility via the network.

2. The method of claim 1, further comprising determining patient-specific anatomical data from the medical image of the bony anatomy of the patient.

3. The method of claim 2, further comprising:
   comparing the patient-specific anatomical data determined from the medical image of the bony anatomy of the patient to historical anatomical data; and
   wherein determining whether the orthopaedic surgical procedure to be performed upon the bony anatomy of the patient is a difficult orthopaedic surgical procedure comprises determining whether the orthopaedic surgical procedure to be performed upon the bony anatomy of the patient is a difficult orthopaedic surgical procedure as a function of comparing the patient-specific anatomical data to historical anatomical data.

4. The method of claim 2, further comprising:
   obtaining a degree of femoral rotation from the patient-specific anatomical data determined from the medical image of the bony anatomy of the patient; and
   comparing the degree of femoral rotation, and determining whether the degree of femoral rotation exceeds a reference threshold degree of femoral rotation.

5. The method of claim 2, further comprising:
   obtaining a tibial slope obtained from the patient-specific anatomical data determined from the medical image of the bony anatomy of the patient; and
   comparing the tibial slope, and determining whether the tibial slope exceeds a reference threshold tibial slope.

6. The method of claim 2, further comprising:
   determining whether a complexity exists as a function of the patient-specific anatomical data determined from the medical image of the bony anatomy of the patient; and
   wherein determining whether the orthopaedic surgical procedure to be performed upon the bony anatomy of the patient is a difficult orthopaedic surgical procedure comprises determining whether the orthopaedic surgical procedure to be performed upon the bony anatomy of the patient is a difficult orthopaedic surgical procedure as a function of determining that a complexity exists.

7. The method of claim 6, wherein determining whether a complexity exists as a function of the patient-specific anatomical data determined from the medical image of the bony anatomy of the patient comprises determining at least one of (i) whether pre-existing metal is present in a surgical area within which the orthopaedic surgical procedure is to be performed upon the bony anatomy of the patient as a function of the patient-specific anatomical data, or (ii) whether an anatomical deformation exists in the bony anatomy of the patient as a function of the patient-specific anatomical data.

8. The method of claim 2, further comprising:
   transmitting the received medical image and the constraint data corresponding to the orthopaedic surgical procedure to be performed upon the bony anatomy of the patient to a remote computing device via the network;
   receiving a recommendation affecting the orthopaedic surgical procedure to be performed upon the bony anatomy of the patient from the remote computing device via the network; and
   wherein generating the second surgical plan for the orthopaedic surgical procedure to be performed upon the bony anatomy of the patient comprise generating the second surgical plan for the orthopaedic surgical procedure to be performed upon the bony anatomy of the patient as a function of the recommendation received from the remote computing device.

9. The method of claim 1, further comprising:
   generating a notification in response to determining that the orthopaedic surgical procedure to be performed upon the bony anatomy of the patient is a difficult orthopaedic surgical procedure; and
   transmitting the generated notification to the computing device of the healthcare facility.

10. The method of claim 1, wherein receiving a medical image of bony anatomy of a patient comprises receiving at least one of a radiographic image, a magnetic resonance imaging image, a computerized tomography image, or a three dimensional ultrasound image.

11. The method of claim 1, wherein the first and second surgical plans comprise at least one of (i) a plurality of ordered surgical steps and instructional images corresponding to the orthopaedic surgical procedure to be performed upon the bony anatomy of the patient; (ii) a recommended orthopaedic implant for use during the orthopaedic surgical procedure to be performed; (iii) an image comprising a digital template of the recommended orthopaedic implant superimposed onto the bony anatomy of the patient in the medical image; (iv) one or more recommended reusable instruments to use during the orthopaedic surgical procedure to be performed; (v) one or more recommended patient-specific instruments to use during the orthopaedic surgical procedure to be performed; (vi) one or more recommended single-use instruments to use during the orthopaedic surgical procedure to be performed; or (vii) one or more videos of surgical procedures performed on other patients having a similar bony anatomy.

12. The method of claim 1, wherein receiving the orthopaedic surgical plan request from the computing device of the healthcare facility via the network comprises receiving the surgical plan request from a surgeon via the computing device of the healthcare facility; and
wherein the method further comprising:
determining whether the surgeon is a registered user of the surgical plan server;
registering the surgeon as a user of the surgical plan server in response to determining that the surgeon is not a registered user;
receiving surgical preference data corresponding to the surgical procedures preferences of the surgeon;
updating surgical preference data in a profile corresponding to the surgeon; and
receiving historical surgical procedure data corresponding to surgical procedures performed by the surgeon.

13. The method of claim 1, further comprising:
receiving surgical procedure results from the computing device of the healthcare facility via the network; and
updating historical anatomical data as a function of the received surgical procedure results.

14. A system for generating a surgical plan for an orthopaedic surgical procedure from medical image data, the system comprising:
a computing device of a healthcare facility to generate an orthopaedic surgical plan request corresponding to an orthopaedic surgical procedure to be performed upon bony anatomy of a patient; and
a surgical plan server of a vendor to (i) receive the orthopaedic surgical plan request from the computing device of the healthcare facility via a network; (ii) receive a medical image of the bony anatomy of the patient upon which the orthopaedic surgical procedure is to be performed from the computing device of the healthcare facility; (iii) receive constraint data corresponding to the orthopaedic surgical procedure to be performed upon the bony anatomy of the patient from the computing device of the healthcare facility; (iv) determine, automatically in response to receiving the medical images and the constraint data, whether the orthopaedic surgical procedure to be performed upon the bony anatomy of the patient is a difficult orthopaedic surgical procedure based on the received medical image and the received constraint data; (v) automatically generate one of: (a) a first surgical plan for the orthopaedic surgical procedure to be performed upon the bony anatomy of the patient in response to determining that the orthopaedic procedure to be performed upon the bony anatomy the patient is not a difficult orthopaedic surgical procedure, or (b) a second surgical plan for the orthopaedic surgical procedure to be performed upon the bony anatomy of the patient in response to determining that the orthopaedic procedure to be performed upon the bony anatomy the patient is a difficult orthopaedic surgical procedure, wherein the second surgical plan is a surgical plan different from the first surgical plan; and (vi) transmit at least one of the first or second surgical plans to the computing device of the healthcare facility via the network.

15. The system of claim 14, wherein the surgical plan server further to determine patient-specific anatomical data from the medical image of the bony anatomy of the patient.

16. The system of claim 15, wherein the surgical plan server further to compare the patient-specific anatomical data determined from the medical image of the bony anatomy of the patient to historical anatomical data; and
wherein to determine whether the orthopaedic surgical procedure to be performed upon the bony anatomy of the patient is a difficult orthopaedic surgical procedure comprises to determine whether the orthopaedic surgical procedure to be performed upon the bony anatomy of the patient is a difficult orthopaedic surgical procedure as a function of comparing the patient-specific anatomical data to historical anatomical data.

17. The system of claim 14, wherein the surgical plan server further to compare a degree of femoral rotation obtained from the patient-specific anatomical data determined from the medical image of the bony anatomy of the patient; and
wherein to determine whether the patient-specific anatomical data determined from the medical image of the bony anatomy of the patient is at least one of outside of a reference range or exceeds a reference threshold comprises to determine whether the degree of femoral rotation obtained from the patient-specific anatomical data exceeds a reference threshold degree of femoral rotation.

18. A system for generating a surgical plan for an orthopaedic surgical procedure from medical image data, the system comprising:
a computing device of a healthcare facility to generate an orthopaedic surgical plan request corresponding to an orthopaedic surgical procedure to be performed upon bony anatomy of a patient; and
a surgical plan server of a vendor to (i) receive the orthopaedic surgical plan request from the computing device of the healthcare facility via a network; (ii) receive a medical image of the bony anatomy of the patient upon which the orthopaedic surgical procedure is to be performed from the computing device of the healthcare facility; (iii) compare a tibial slope obtained from patient-specific anatomical data determined from the medical image of the bony anatomy of the patient; (iv) receive constraint data corresponding to the orthopaedic surgical procedure to be performed upon the bony anatomy of the patient from the computing device of the healthcare facility; (v) determine whether the orthopaedic surgical procedure to be performed upon the bony anatomy of the patient is a difficult orthopaedic surgical procedure based on the received medical image and the received constraint data; (vi) generate one of: (a) a first surgical plan for the orthopaedic surgical procedure to be performed upon the bony anatomy of the patient in response to determining that the orthopaedic procedure to be performed upon the bony anatomy the patient is not a difficult orthopaedic surgical procedure, or (b) a second surgical plan for the orthopaedic surgical procedure to be performed upon the bony anatomy of the patient in response to determining that the orthopaedic procedure to be performed upon the bony anatomy the patient is a difficult orthopaedic surgical procedure, wherein the second surgical plan is a surgical plan different from the first surgical plan; and (vi) transmit at least one of the first or second surgical plans to the computing device of the healthcare facility via the network, wherein to determine whether the patient-specific anatomical data determined from the medical image of the bony anatomy of the patient is at least one of outside of a reference range or exceeds a reference threshold comprises to determine whether the tibial slope obtained from the patient-specific anatomical data exceeds a reference threshold tibial slope.

19. The system of claim 18, wherein the surgical plan server further to determine whether a complexity exists as a function of the patient-specific anatomical data determined from the medical image of the bony anatomy of the patient; and wherein to determine whether the orthopaedic surgical procedure to be performed upon the bony anatomy of the patient is a difficult orthopaedic surgical procedure comprises to determine whether the orthopaedic surgical procedure to be performed upon the bony anatomy of the patient is a difficult orthopaedic surgical procedure as a function of determining that a complexity exists.

20. The system of claim 18, further comprising:

a remote computing device to (i) receive the medical image and the constraint data corresponding to the orthopaedic surgical procedure to be performed upon the bony anatomy of the patient from the surgical plan server via the network; (ii) generate a recommendation affecting the orthopaedic surgical procedure to be performed upon the bony anatomy of the patient; and (iii) transmit the recommendation affecting the orthopaedic surgical procedure to be performed upon the bony anatomy of the patient to the surgical plan server via the network;

wherein the surgical plan server further to receive the recommendation affecting the orthopaedic surgical procedure to be performed upon the bony anatomy of the patient from the remote computing device; and wherein to generate the second surgical plan for the orthopaedic surgical procedure to be performed upon the bony anatomy of the patient comprises to generate the second surgical plan for the orthopaedic surgical procedure to be performed upon the bony anatomy of the patient as a function of the recommendation received from the remote computing device.

* * * * *